(12) United States Patent
Al-Hariri et al.

(10) Patent No.: US 12,150,964 B1
(45) Date of Patent: *Nov. 26, 2024

(54) SUBCUTANEOUS INJECTION METHOD FOR PAIN TREATMENT

(71) Applicant: Imam Abdulrahman Bin Faisal University, Dammam (SA)

(72) Inventors: Mohammed Taha Ali Al-Hariri, Dammam (SA); Turki Saeed Mohammed Abualait, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/780,575

(22) Filed: Jul. 23, 2024

Related U.S. Application Data (63) Continuation of application No. 18/636,861, filed on Apr. 16, 2024, now Pat. No. 12,076,349, which is a continuation of application No. 17/362,083, filed on Jun. 29, 2021, now Pat. No. 11,998,572.

(51) Int. Cl.

| | | |
|---|---|---|
| *A61K 35/644* | (2015.01) | |
| *A61K 9/70* | (2006.01) | |
| *A61K 45/06* | (2006.01) | |
| *A61N 5/06* | (2006.01) | |
| *A61P 29/02* | (2006.01) | |

(52) U.S. Cl.
CPC .......... *A61K 35/644* (2013.01); *A61K 9/7007* (2013.01); *A61K 45/06* (2013.01); *A61N 5/0616* (2013.01); *A61P 29/02* (2018.01); *A61K 2236/333* (2013.01); *A61K 2236/35* (2013.01); *A61N 2005/0661* (2013.01)

(58) Field of Classification Search
CPC .......... A61N 5/0616; A61N 2005/0661; A61N 5/062; A61N 5/0622; A61K 2236/333; A61K 2236/35; A61K 35/644; A61K 45/06; A61K 9/7007; A61P 29/02

See application file for complete search history.

(56) References Cited

U.S. PATENT DOCUMENTS

| | | |
|---|---|---|
| 7,618,946 B2 | 11/2009 | Quinn |
| 2022/0118035 A1 | 4/2022 | Buzzi |

FOREIGN PATENT DOCUMENTS

| | | |
|---|---|---|
| BR | PI 0900802-0 B1 | 3/2020 |
| CN | 107412138 A | 12/2017 |
| KR | 10-2019-0037926 | 4/2019 |

OTHER PUBLICATIONS

Santos, et al. ; Anti-inflammatory and antinociceptive effects of Baccharisdracunculifolia DC (Asteraceae) in different experimental models ; Journal of Ethnopharmacology vol. 127, Issue 2 ; Feb. 3, 2010 ; pp. 543-550 ; 3 Pages.
Laranjeira, et al. ; Baccharis dracunculifolia decreases nociception, depressive-like behaviour andsupraspinal activated microglia in rats with experimental monoarthritis ; Planta Medica International Open 2017 ; 2 Pages.
Paulino, et al. ; Evaluation of the Analgesic and ANto-Inflammatory Effects of a Brazilian Green Propolis ; Planta Med ; Jun. 1, 2006 ; 8 Pages.
Szliszka, et al. ; Chemical Composition and Anti-Inflammatory Effect of Ethanolic Extract of Brazilian Green Propolis on Activated J774A.1 Macrophages ; Hindawi Publishing Company ; Evidence-Based Complementary and Alternative Medicine 2013 ; 14 Pages.
Freires, et al. ; A pharmacological perspective on the use of Brazilian RedPropolis and its isolated compounds against human diseases ; European Journal of Medicinal Chemistry, vol. 110 ; Mar. 3, 2016 ; pp. 267-279 ; 4 Pages.
Hata T, Tazawa S, Ohta S, Rhyu M-R, Misaka T, et al. (2012); "Artepillin C, a Major Ingredient of Brazilian Propolis, Induces a Pungent Taste by Activating TRPA 1 Channels." PLoS One 7(11): e48072. doi :10.1371/journal.pone.0048072; published Nov. 2, 2012.
Yam et al.; "General Pathways of Pain Sensation and the Major Neurotransmitters Involved in Pain Regulation"; Int. J. Mol. Sci. ( 2018), 19, 2164; published Jul. 24, 2018.
Dr. Balasaraswathy P.; "Skin Care N Cure"; published online Nov. 3, 2014; https://www.skincarencure.com/author/skincarencure_bggy5h/; 11-pg pdf.

*Primary Examiner* — Jeffrey T. Palenik
(74) *Attorney, Agent, or Firm* — Oblon, McClelland, Maier & Neustadt, L.L.P.

(57) ABSTRACT

A method for treating or preventing nociceptive pain by administering an ethanol extract of Brazilian green propolis and compositions comprising this extract.

10 Claims, 7 Drawing Sheets

FIG. 1

*infrared test*

FIG. 2

*formalin-induced pain*

FIG. 3

*Abdominal writhing test*

SUBCUTANEOUS INJECTION METHOD FOR PAIN TREATMENT

CROSS-REFERENCE TO RELATED APPLICATIONS

The present application is a Continuation of U.S. application Ser. No. 18/636,861, now allowed, having a filing date of Apr. 16, 2024 which is a Continuation of U.S. application Ser. No. 17/362,083, now U.S. Pat. No. 11,998,572, having a filing date of Jun. 29, 2021.

BACKGROUND OF THE INVENTION

Field of the Invention

The invention pertains to the fields of medicine, pain management, and apiculture.

Related Art

Pain is an uncomfortable feeling that involves motivational, cognitive and affective aspects which serves as an alarm to minimize contact with a harmful agent. See Ruel, H. L.; Steagall, P. V. *Adjuvant analgesics in acute pain management.* VET. CLIN. SMALL ANIM. PRACT. 2019, 49, 1127-1141.

Pain is initiated by nociceptors or specialized peripheral sensory neurons which are found in muscle, cutaneous tissues, connective tissues, vessels, viscera and bone; Zakaria, Z. A.; et al. *Antinociceptive activity of petroleum ether fraction obtained from methanolic extract of Clinacanthus nutans leaves involves the activation of opioid receptors and NO-mediated/cGMP-independent pathway.* BMC COMPLEMENT. ALTERN. MED. 2019, 19, 79. These nociceptors are activated by noxious stimuli including by chemical, mechanical and thermal stimuli that trigger appropriate response to tissue damage or injury. However, when pain persists, it affects the quality of life of a person who suffers from it; Goucke, C. R. & Chaudakshetrin, P. *Pain: A neglected problem in the low-resource setting.* ANESTH. ANALG. 2018, 126, 1283-1286.

Conventional pain management techniques include the administration of analgesics and anti-inflammatory agents; De Moraes, S. Z.; et al. *Antinociceptive and anti-inflammatory effect of Poincianella pyramidalis (Tul).* LP QUEIROZ. J. ETHNOPHARMACOL. 2020, 254, 112563. However, these agents often exhibit detrimental side-effects. For example, non-steroidal anti-inflammatory drugs (NSAIDS) can induce severe or life-threatening gastrointestinal (GI) bleeding, cause ulcers or increase the risk of heart attacks or strokes. NSAIDS also can produce other undesirable or toxic side effects on the gastric system (stomach and intestines), liver and kidneys.

Due to adverse effects or toxicities associated with conventional pain therapy, there is a need for the identification and development of new and effective agents with no or fewer undesirable side effects; De Souza Sampaio, R.; et al., *Antinociceptive activity of the Psidium brownianum Mart ex DC. leaf essential oil in mice.* FOOD CHEM. TOXICOL. 2020, 135, 111053, incorporated herein by reference in its entirety.

Natural products have been pursued as possible alternatives to conventional analgesics; Islam, N. U. et al., *Antinociceptive, muscle relaxant and sedative activities of gold nanoparticles generated by methanolic extract of Euphorbia milii.* BMC COMPLEMENT. ALTERN. MED. 2015, 15, 1-11. Such natural products are often readily available in areas that are underserved by conventional pharmaceutical medicines.

In the last three decades, led by the World Health Organization (WHO), interest in natural products has greatly increased. The WHO recently published a document entitled *WHO traditional medicine strategy:* 2014-2023, in which it endorsed and supported the development and implementation of action plans to strengthen the role traditional medicines in public health; World Health Organization. WHO TRADITIONAL MEDICINE STRATEGY: 2014-2023; World Health Organization: Geneva, Switzerland, 2013.

Different chemical compounds, such as particular flavonoid or phytochemicals, having potent analgesic effects have been obtained from natural sources. Such natural analgesics have been explored as possible lead compounds for the development of new analgesic drugs; Abdel-Rahman, R. F. *Natural products as a source for novel analgesic compounds.* PAIN RELIEF ANALG. ALTERN. THER. INTECH OPEN 2017, 277-299.

Propolis (bee glue) is a natural resinous mixture produced by honey bees which is produced when bee-released compounds are combined with exudates gathered from various plant sources; Al-Hariri, M. T. *Propolis and its direct and indirect hypoglycemic effect.* J. FAM. COMMUNITY MED. 2011, 18, 152. Propolis may be fractionated by various means including by production of propolis extracts in different solvents such as water, ethanol or oil.

As disclosed herein, the inventors investigated and explored potential analgesic properties of propolis on nociceptive pain. As disclosed herein, the inventors describe the identification, formulation and use of different fractions or extracts of Brazilian green propolis as agents to ameliorate nociceptive pain or exhibit other analgesic properties.

SUMMARY OF THE INVENTION

One aspect of the disclosure is a method for preventing or treating nociceptive pain comprising, consisting essentially of, or consisting of, applying an ethanol extract of Brazilian green propolis ("BGP") to a site at risk of thermal injury or to a burn. In some embodiments this method further comprises applying a mixture of both an ethanol and an oil extract of BGP to a site at risk of thermal injury or to a burn.

Another aspect of the invention is directed to a composition comprising, consisting essentially of, or consisting of an ethanol extract of BGP or a material derived from such an extract in a form suitable for application to a site at risk of thermal injury or to a burn. This composition may further comprise an oil extract of BGP or a material obtained from such an oil extract. The composition may also contain other active ingredients such as NSAIDs or opioid analgesics or be prepared as part of a wound or burn dressing.

One aspect of the invention is a method for preventing or treating pain, or more specifically, nociceptive pain from a burn or thermal injury comprising administering to a subject in need thereof a composition comprising an ethanol extract of Brazilian green propolis ("BGP"). Preferably, the method is directed to treating non-inflammatory pain or early phase responses mediated by C-fiber activation.

The organization of rodent dorsal horn laminae is largely similar to that in humans which is why animal model is similar to human; see Kaliyaperumal, S. et al., TOXICOLOGICAL PATHOLOGY, 2019, 48, 202-219; Zotova, E. G. et al., PHYSIOLOGY JOURNAL, 2013, Article ID 254789; and Serra, J. et al., PAIN, 2012, 153(1)m 42-55 each incorporated by reference.

Nerve endings of nociceptive C fibers (nociceptors) are capable to translate an aggressive thermic, chemical, or mechanical stimulus into an electrical stimulus that will be transmitted to the central nervous system and interpreted in the cerebral cortex as pain. However, in the intact animal and in humans, nociceptive input reaches subcortical and cortical brain nuclei that contribute to the affective, aversive states of pain. Hypertext transfer protocol secure://www.ncbi.nlm.nih.gov/books/NBK32655/.

In another embodiment, the pain or nociceptive pain further comprises late phase response resulting from an inflammatory response in combination with activation of N-methyl-d-aspartate (NMDA) and non-NMDA receptors and NO cascade).

Over the past few years, a number of animal models have been developed that, to a large extent, mimic the nociception originating in the viscera; Larauche, M., et al., EXP. NEUROL. (in press); Al-Chaer, E. D. et al., PAIN, 2002, 96(3), 221-225. These models have helped advance our understanding of the acute physiological responses associated with mechanical or inflammatory visceral nociception. It has become apparent that visceral pain and somatic pain are different, although some similarities exist; Al-Chaer et al, supra. In the present study, used the acetic acid-induced nociceptive model was developed for the screening of analgesic drugs and described as the writhing test to exam the anti-nociceptive effect of minocycline in acute visceral pain. I.p. injection of acetic acid is a well-known noxious chemical visceral stimulus in animals; Koster, R, et al., FED PROC, 1959, 18, 412. The nociceptive stimulation of the peritoneum by i.p. acetic acid produces abdominal contractions or writhes, and gastrointestinal ileus characterized by inhibition of gastric emptying and small intestine transit. Both procedures are associated with visceral pain. This model is also used as a model of somatic-visceral pain; Ghia, et al., LIFE SCI, 2004, 75, 1787-1799.

In preferred embodiments of this method, the BGP ethanol extract is prepared by extracting BGP with an aqueous solution containing 5 to 100 vol. % of ethanol, preferably from 60-80 vol. % ethanol.

In some embodiments, the composition further composition further comprises an oil extract of BGP in combination with an ethanol extract. In an alternative embodiment, the method may be practiced with a composition comprising an oil extract of BGP.

In some embodiments the composition further comprises, or comprises, a vegetable oil extract of BGP.

In other embodiments, the composition used in the method disclosed herein comprises extract of BGP that has been emulsified with the ethanol extract and/or oil extract of BGP.

In further embodiments, the disclosed method may use a composition further comprises a NSAID, an opioid, or other analgesic or anesthetic.

In other embodiments, the composition used in the disclosed method further comprises a sunblock or sunscreen and is topically administered to the subject. In one embodiment, the composition comprises a hydrogel.

In one embodiment, the composition comprises an emulsion or liposomes which may comprise an oily and/or aqueous phase containing the ethanol and/or oil extract of BGP.

In another embodiment, the composition comprises a sunscreen or sunblock.

Another aspect of the disclosure is directed to a burn dressing comprising an ethanol and/or oil extract of BGP.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

As explained above, new treatment strategies and therapeutics for treating nociceptive pain are needed because conventional pain management techniques and pharmaceuticals do not adequately treat different types of nociceptive pain and/or have undesirable side-effects. With this objective in mind, the inventors sought to identify new treatment strategies for nociceptive pain management using natural materials derived from Brazilian green propolis (BGP). Specifically, as disclosed herein, the properties of ethanol extracts of Brazilian green propolis were evaluated using a variety of in vivo models of different types of nociceptive and inflammatory pain. Among other findings, the results demonstrated that BGP ethanol extracts significantly reduced visceral nociceptive pain, increased the pain threshold against pain induced by infrared radiation, and inhibited chemically (formalin) induced pain. Administration of BGP extract reduced both non-inflammatory nociceptive pain as well as some types of inflammatory nociceptive pain.

The BGP compositions used in the presently disclosed method may be administered in a form suitable for ameliorating or reducing the severity of nociceptive pain. In some embodiments, the composition is topically administered to the subject; in other embodiments the composition is administered to the subject prior to a burn; in another embodiment the composition is administered to a subject at risk of being burned and who handles or works around hot liquids, hot surfaces, or flames.

Another aspect of the disclosure is directed to a formulation comprising an ethanol extract and/or oil extract of BGP and an excipient suitable for application to the skin or to a burn. Such a composition preferably comprises a gel or spray which may further comprise other active ingredients such as s an NSAID, opioid, analgesic or anesthetic.

Brazilian green propolis. Propolis is formed by a complex set of components collected by *Apis mellifera* bees from different parts of plant resins (e.g., twigs, flowers, pollen, buttons, and exudates of trees) which are deposited in the hive with saliva and enzymes of the insect to seal cracks and maintain the temperature in the hive. Standardized Brazilian green propolis products are commercially available, such as those sold by Apis Flora Company (hypertext protocol secure://www.apisflora.com.br/catalog last accessed Apr. 14, 2021). Green propolis may be harvested from hives in the Brazilian states or regions of Minas Gerais (southeast) or Parana (south) or other states or regions of Brazil.

Propolis comprises resins with about 40-60 wt % of the mixture being composed of flavonoids and phenolic acids usually about 50 wt %; about 25-35 wt % waxes, usually about 30 wt %; about 5-15 wt % essential oils usually about 10 wt %; and about 1-10 wt % pollen, usually about 5 wt %. Propolis can be composed of hydrocarbons, alcohols, aliphatic and aromatic acids, esters and its derivatives, aldehydes, ketones, flavonoids, fatty acids, terpenoids, amino acids, sugars, lignans, vitamins, minerals, and other components.

An ethanol extract may contain various concentrations of flavonoid class, prenylated derivatives of p-coumaric acid, coumaric and ferulic acid, pinobanksin, isosakuretin and kaempferide, isopentenylated phenylpropanoids and their derivatives, caffeoylquinic acids, some terpenes, phenolic acids and has an especially high level of Artepillin C (3,5-diisopentenyl-4-hydroxycinnamic acid); as described by and incorporated by reference to Simoes, L. M. C. et al., J. ETHNOPHARMACOLOGY, 2004, 94(1), 59-65.

The chemical composition of propolis differs significantly according to the geographic region where resins were collected due to the flora of each region, allowing the selection of different plants as source of resin. When this product is derived from Europe or China, for example, the main plant metabolites found are flavonoids and phenolic acids, unlike BGP s from southeastern Brazil, which, besides phenolic compounds, contain high amounts of terpenoids and prenylated derivatives of p-coumaric acid such as those shown by FIGS. 4A and 4B.

These differences in composition reveal the collection of resinous material in temperate zones from poplar, especially species of *Populus*; and in southeastern Brazil from *Baccharis dracunculifolia* DC (Compositae), *Baccharis dracunculifolia* DC (Asteraceae) is the main botanical source used by honeybees to produce Brazilian green propolis.

Brazilian green propolis is composed of large amounts of phenolic compounds such as Artepillin C, baccharin, kaempferide, isosakuranetin, dihydrokaempferide, drupanin, p-coumaric acid, caffeic acid, aromadendrin, caffeoylquinic acid derivatives, and other compounds, such as the triterpene lupeol-3-(3'R-hydroxy)-hexadecanoate. The key source of these compounds is *B. dracunculifolia*.

Figure 4A:
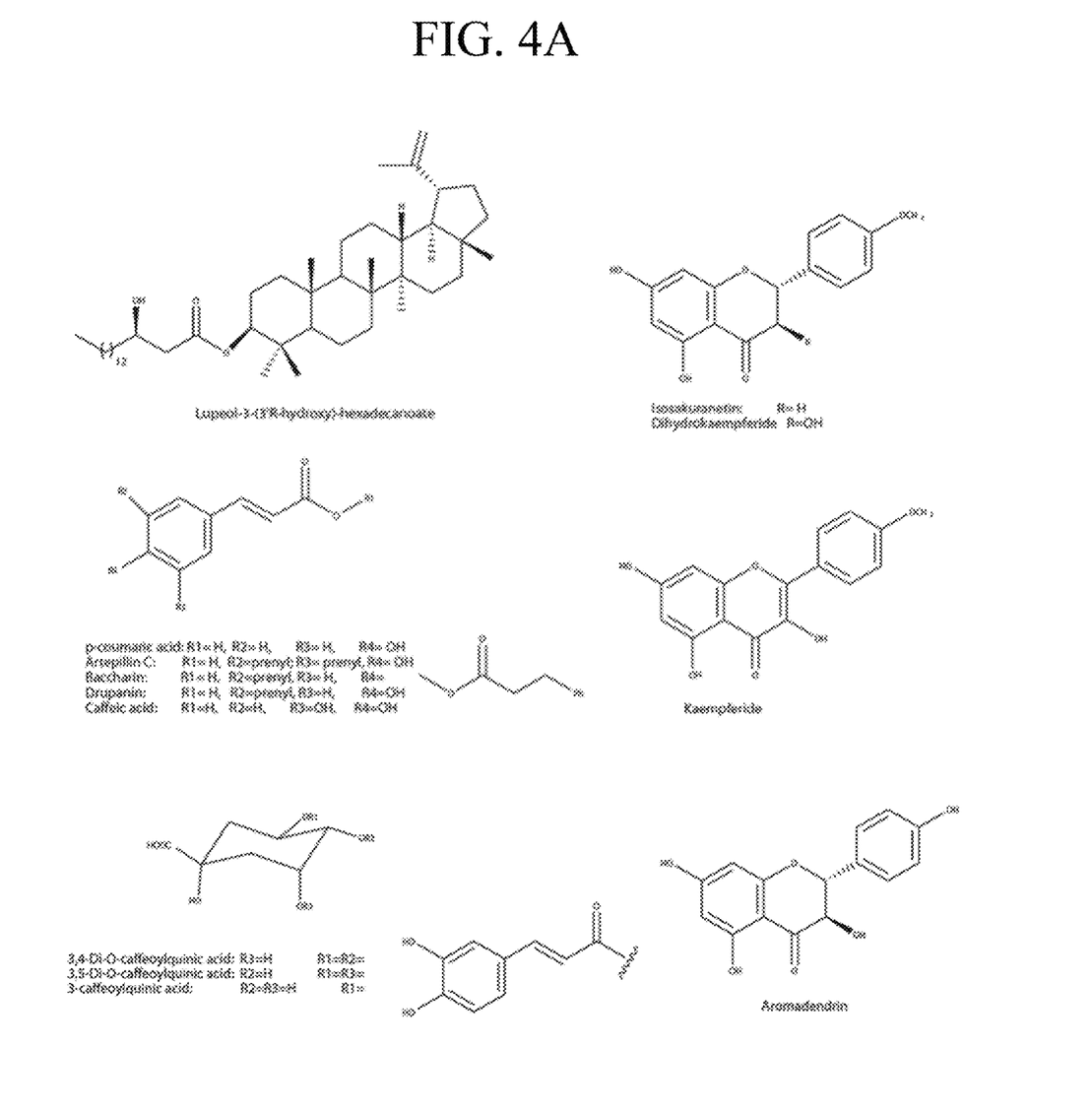
FIG. 4A describes certain chemical structures of components of Brazilian green propolis.
Figure 4B:
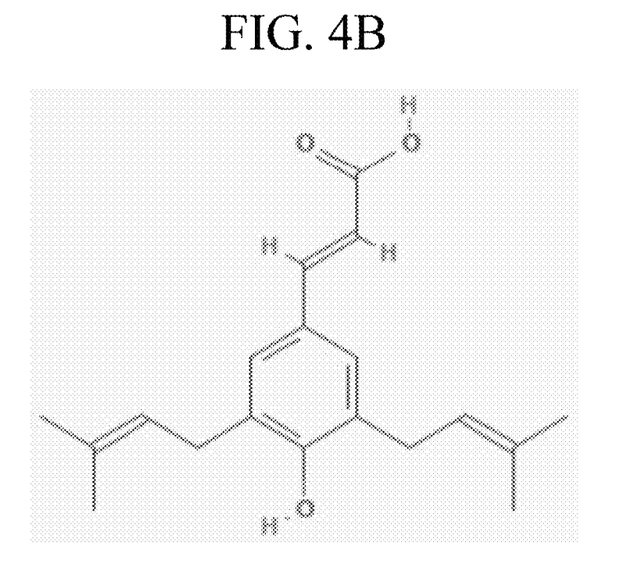
FIG. 4B describes the chemical structure of Artepillin C.
Figure 5:
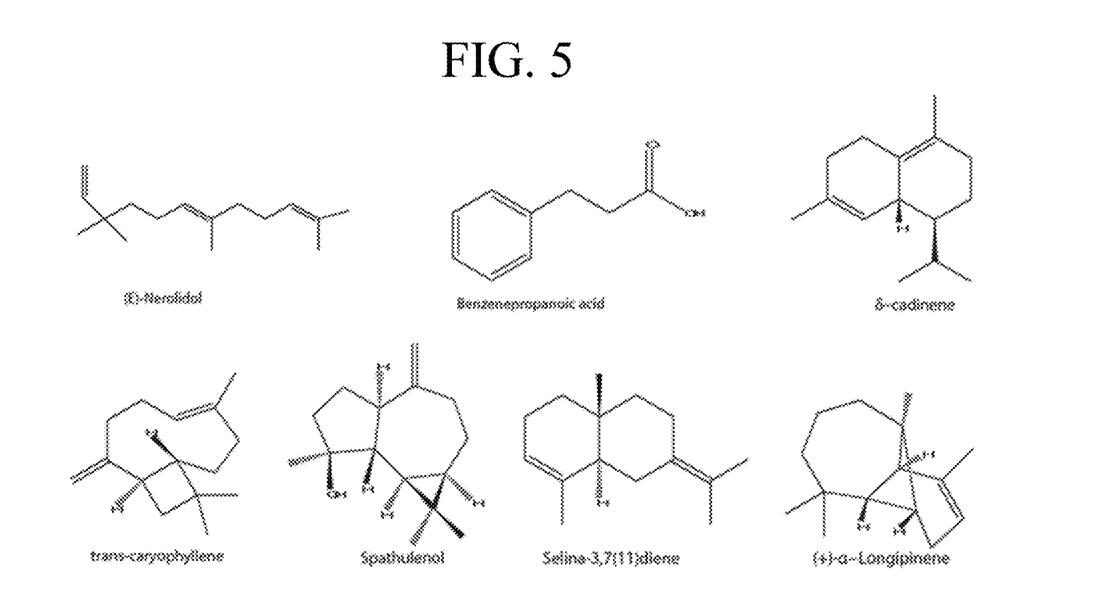
FIG. 5 describes the chemical structures of certain volatile components of Brazilian green propolis.

FIG. 4A describes the chemical structures of compounds found in Brazilian green propolis and FIG. 4B describes the chemical structure of Artepillin C a component of Brazilian green propolis. The major volatile components of Brazilian green propolis are sesquiterpenes, such as (E)-nerolidol, β-caryophyllene, spathulenol, and δ-cadinene; FIG. 5. Furthermore, other compounds such as selina-3,7(11)diene, benzenepropanoic acid and longipinene were also identified. According to Fernandes-Silva, C. C., et al., J. Sci. Food Agric, 2015, 95, 309105, the main constituents of a volatile fraction of BGP are the phenylpropanoid 3-prenylcinnamic acid allyl ester (26.3%) and the sesquiterpene spathulenol (23.4%). It also contains several other sesquiterpenes and phenylpropanoids, in addition to linalool and α-terpineol (monoterpenes). Such volatile components may be extracted into water, ethanol or other alcohol, oil, or other solvent.

Figure 6:
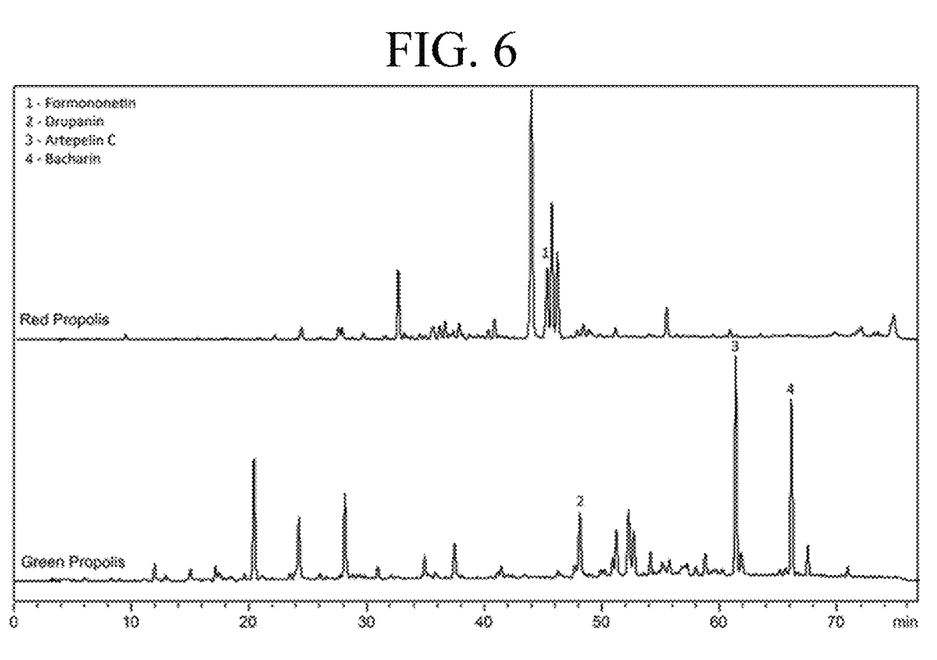
FIG. 6 describes the differences in the chromatographic chemical fingerprints of red and green propolis.
Figure 7:
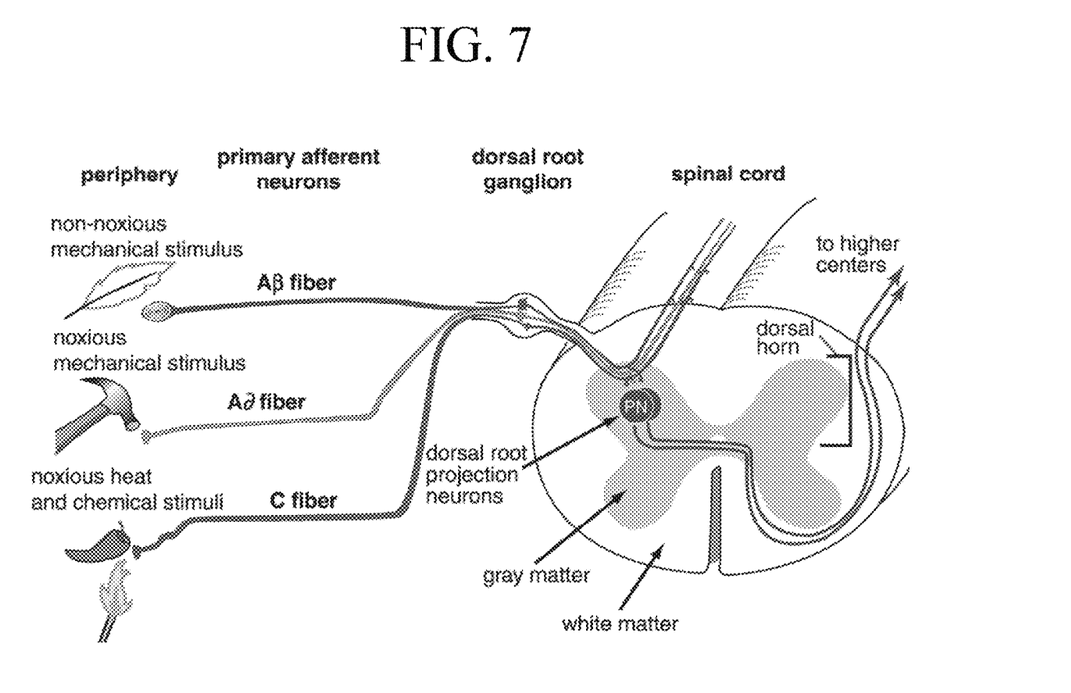
FIG. 7 describes nociceptive pain fibers and pathways.

As shown by FIG. 6, Brazilian green propolis contains little or no formononetin but contains significant amounts of drupanin, Artepillin C and bacharin compared to red propolis. See Berretta, A. A., et al., *Functional Properties of Brazilian Propolis: From Chemical Composition Until the Market,* 2017, DOI: 10.5772/65932. Available from: hypertext transfer protocol secure://www.intechopen.com/books/superfood-and-functional-food-an-overview-of-their-processing-and-utilization/functional-properties-of-brazilian-propolis-from-chemical-composition-until-the-market (last accessed Apr. 2, 2021, incorporated by reference for its description of the chemical composition of, functional properties of, distinguishing features of green propolis compared to other types of propolis, such as red or brown propolis, sources of, production of, and other description of Brazilian propolis. Those skilled in the art can determine the content ranges of these and other components of BGP in commercially available BGP, such as those available from the Apis Flora Co.

The concentrations (wt/vol or wt/wt) of each these components, including Artepillin C, in a water, ethanol, or oil extract as described herein, may be <10, 10, 20, 30, 40, 50, 60, 70, 80, 90, 100, 200, 300, 400 or >400% more than those found in raw BGP.

Brazilian green propolis water extract. A water extract as described herein includes those made using an aqueous solution, preferably a solution with no or substantially no ethanol. An aqueous solution may contain salts, buffers, acids or bases or other water-soluble components. It may be produced in a manner similar to that described below for an ethanol extract.

Brazilian green propolis ethanol extract. An ethanol extract is produced by extracting BGP in a solvent containing ethanol. BGP alcohol extracts may be produced by extracting BGP in other alcohols or aqueous alcohols, such as those containing methanol, propanols, butanols, or combinations of alcohols. Water or an aqueous buffer may be present. Methods for producing extracts of BGP, including ethanol extracts, are described by and incorporated by reference to Devequi-Nunes D, et al., *Chemical characterization and biological activity of six different extracts of propolis through conventional methods and supercritical extraction. PLoS ONE,* 2018, 13(12): e0207676. To prepare an ethanol extract, BGP may be processed by chopping, grinding, milling, powdering or otherwise disintegrating prior to extraction to provide a larger surface area and smaller particle volume for extraction. An extract may be produced by dissolving soluble components of BGP in a mixture of water and alcohol.

Ethanol is a very polar molecule due to its hydroxyl (OH) group, with the high electronegativity of oxygen allowing hydrogen bonding to take place with other molecules. Ethanol therefore attracts polar and ionic molecules. The ethyl ($C_2H_5$) group in ethanol is non-polar. Ethanol therefore attracts non-polar molecules. The inventors considered that an ethanol extraction might separate or concentrate ethanol-soluble components of BGP that exhibit analgesic effects, especially on early phase nociceptive pain, from other inactive or pain-inducing components of BGP.

A concentration of ethanol suitable for extracting analgesic compounds from BGP may be selected by one skilled in the art and such extracts assessed for activity as disclosed herein. Such a mixture may comprise about <5, 10, 20, 30, 40, 50, 60, 70, 80, 90, 95 or >95% (vol/vol) ethanol with the balance being water or an aqueous solution or buffer such as normal saline, phosphate-buffered saline (PBS), Tris buffer, or other aqueous solution, preferably a physiologically acceptable solution. Preferably, a concentration of ethanol ranging from 40 to 70% or 50, 55 to 60% (vol/vol) is employed.

The extraction may be performed at a pH ranging from <4, 4, 5, 6, 7, 8, 9, 10, or >10, preferable at a pH from about 6, 6.5, 7, 7.5 to 8. The pH may be adjusted by known methods, such as by addition of, or titration with, an acid, such as HCl, or a base, such as NaOH. The pH may also be adjusted or stabilized by addition of a buffer, such as Tris. Buffers with particular pH buffering ranges, including MES, ACES, PIPES, HEPES, Tricine, Gly-Gly, CAPS, CABS, and others are commercially available and incorporated by reference to hypertext transfer protocol secure://www.sigmaaldrich.com/life-science/core-bioreagents/biological-buffers/learning-center/buffer-reference-center.html #selected buffers.

An ethanol extract of BGP may include phenolic compounds, flavonoids, and antioxidants. Representative compounds include Artepillin C, 2,2-diphenyl-1-picrylhydrazyl (DPPH), p-coumaric acid, and 2'-azinobis-(3-ethylbenzothiazoline-6-sulfonic acid (ABTS). The extracts disclosed herein may be produced or stored under an inert atmosphere, such as nitrogen or a noble gas, or in the absence of oxygen. Extracts may be stored at a temperature <0, 4, 5, 10, 20, 25 or >25° C., preferably below room temperature.

Standardization of an ethanolic extract of BGP may be based on the content of these or other compounds as they appear in raw propolis, its volatile components, or its fractions. For example, a standardized extract may contain a reference amount of Artepillin C or phenol compounds or flavinoids.

Ethanol extracts of BGP contain a high content of flavonoids and Artepillin C as described by and incorporated by reference to Shahinozzaman, M. FITOTERAPIA, 2020, 147, 104775. These compounds may be associated with analgesic activity.

Ethanol extracts of Brazilian green propolis are commercially available (e.g., from Uniflora, hypertext protocol secure://www.uniflora.us/, last accessed Apr. 21, 2021, incorporated by reference). Uniflora catalog numbers include Item #19150 (BRAZILIAN GREEN BEE PROPOLIS LIQUID EXTRACT ALCOHOL FREE 60 BRIX), Item #19125 (BRAZILIAN GREEN BEE PROPOLIS LIQUID EXTRACT 35%); Item #191130 (BRAZILIAN GREEN BEE PROPOLIS LIQUID EXTRACT MEDIUM TYPE 45%); and Item #19140 (BRAZILIAN GREEN BEE PROPOLIS LIQUID EXTRACT STRONG TYPE 55%). These commercial extracts contain components extracted from BGP using ethanol.

Commercially available ethanol extracts of BGP contain caffeic acid, p-coumaric acid, trans-cinnamic acid, aromadendrin and Artepillin C. In some embodiments, one or more of these components of an ethanol extract may be used alone or in mixture with other such components or in combination with ethanol extract of BGP (fortification), in a method as disclosed herein.

In some embodiments, an ethanol or water extract of BGP is desiccated or freeze dried to remove solvents to produce a solid material. This solid material may be resuspended in a solute of choice, preferably a physiological solute such as normal saline or PBS for administration. In other modes the solid material may be administered as a solid, for example, in a capsule or tablet or as a troche. An ethanol, water, or oil extract may be further processed to extract particular components of the extract.

In some alternate embodiments, other alcohols, such as methanol, propanol or pentanol or hexanol may be used to produce an alcoholic extract of BPG. Ethanol is considered a universal solvent, as its molecular structure allows for the dissolving of both polar, hydrophilic and nonpolar, hydrophobic compounds. As ethanol also has a low boiling point, it is easy to remove from a solution that has been used to dissolve other compounds, making it a popular extracting agent for botanical oils. In ethanol the $C_2H_5$ moiety is hydrophobic, but the OH group is polar giving rise to a dipole moment. The OH group can act as a hydrogen bond donor and a hydrogen bond acceptor with water. As the length of the alkyl chain increases, the hydrophobic effect increases, thus while methanol, ethanol, propanol are miscible with water, higher alcohols such as butanol (0.11 alcohol solubility in water), pentanol (0.030), hexanol (0058), and heptanol (0.0008) are much less so and after heptanol, the higher alcohols are considered immiscible.

Similar proportions of water and alcohol to those described above may be used during extraction. Preferably a water miscible alcohol, such as methanol or propanol is selected, however, in some embodiments water immiscible alcohols (or other immiscible solvents) may be used to extract BGP and extract materials recovered from either a water phase or alcohol phase. BGP may also be extracted using supercritical carbon dioxide. Sources of BGP and extraction methods including using ethanol or supercritical carbon dioxide are described by and incorporated by reference to Machado, et al., hypertext transfer protocol secure://www.ncbi.nlm.nih.gov/pmc/articles/PMC4706314 2016; 11(1): e0145954. As explained below, BGP may also be extracted using non-polar or hydrophobic solvents.

Surprisingly, in view of the presence of Artepillin C, the inventors found that an ethanol extract of BGP inhibits nociceptive pain because ethanol extracts. Artepillin C (FIG. 4B) is a compound that activates TRPA1 which is an ion channel sensor for pain, cold and itch; see Hata, T. et al., *Artepillin C, a major ingredient of Brazilian propolis, induces a pungent taste by activating TRPA1 channels*, PLoS ONE. 2012; 7(11):e48072. doi: 10.1371/journal.pone.0048072. Epub 2012 Nov. 2. TRPA1 is an ion channel located on the plasma membrane of many human and animal cells. This ion channel is best known as a sensor for pain, cold and itch in humans and other mammals, as well as a sensor for environmental irritants giving rise to other protective responses (tears, airway resistance, and cough); see Andersen H H, et al. *Human Surrogate Models of Histaminergic and Non-histaminergic Itch*, ACTA DERMATO-VENEREOLOGICA. 2015, 95 (7): 771-7. doi:10.2340/00015555-2146. PMID 26015312; and Højland C R, et al., *A human surrogate model of itch utilizing the TRPA1 agonist trans-cinnamaldehyde*. ACTA DERMATO-VENEREOLOGICA. 2015, 95 (7): 798 803. doi:10.2340/00015555-2103. PMID 25792226.

While not being bound to any theory or explanation, the inventors believe that components in an ethanol extract such as Artepillin C or other flavonoid compounds such as pinobanksin and kaempferol and the phenolic acides3,5-diprenyl-4-hydroxcinnamic acid,2,2-dimethyl-6-carboxyethenyl-8-prenyle-2H-1-benzopyran and 3-prenyl-4-hydroxycinnamic may produce analgesic effects via inhibition of inducible NOS (iNOS) activity.

Brazilian green propolis oil extract: The Brazilian green propolis oil extract as used herein typically comprises a vegetable oil extract of Brazilian green propolis. However, in some embodiments mineral oils or other hydrophobic or non-ionic solvents may be used. In a preferred embodiment, the Brazilian green propolis extract comprises canola oil. An oil extract of GPB may contain Hydroxy-3-prenylcinnamic acid, 3,4-Dihydroxy-5-prenylcinnamic acid Isosakuranetin, Kaempferide, Dihydrokaempferide, and (E)-3-{-4-hydroxy-3-[(E)-4-(2,3-dihydrocinnamoyloxy)-3-methyl-2-butenyl]-5-prenylphenyl}-2-propenoic acid as well as Artepillin C. These and other components of GPB oil extract and their properties aredescribed by, and incorporated by reference to see Cavalho, et al., *In vivo antitumoural activity and composition of an oil extract of Brazilian propolis*, FOOD CHEMISTRY, 2011, 126(3), 1239-1245, and Shahinozzaman, et al., *Artepillin C: A comprehensive review of its chemistry, bioavailability, and pharmacologicalproperties*, FITOTERAPIA, 2020, 147, 104775.

The components of Brazilian green propolis that are extracted into the oil (or water or ethanol) may be further isolated, for example, by chromatography or phase-partitioning. One example is partitioning of Brazilian green propolis oil in an alcohol or aqueous mixture of an alcohol substantially immiscible with the oil, and recovery of the fraction of propolis compounds partitioning into the aqueous alcohol. The isolated fraction of Brazilian green propolis may be used by itself, resuspended in oil, or admixed with other carriers or excipients.

In some embodiments, the Brazilian green propolis oil extract or ethanol extract comprises 0.01, 0.02, 0.05, 0.1, 0.2, 0.5, 1.0, 2.0 to 5 wt % of phenolic acids or other phenolic compounds. This range, and other ranges disclosed herein, include all intermediate and terminal values as well as subranges.

In other embodiment the Brazilian green propolis oil extract or ethanol extract comprises 00.01, 0.02, 0.05, 0.1, 0.2, 0.5, 1.0, 2.0 to 5 wt % of flavonoids.

In one embodiment, the Brazilian propolis oil extract or ethanol extract comprises 0.01, 0.02, 0.05, 0.1, 0.2, 0.5, 1.0, 2.0 to 5 wt % of Artepillin C.

Other extracts of BGP. In some embodiments, other extracts of BGP may be used, for example, those extracted in hydroxy-3-prenylcinnamic acid, 3,4-dihydroxy-5-prenylcinnamic acid, isosakuranetin, kaempferide, dihydrokaempferide, and (E)-3-{-4-hydroxy-3-[(E)-4-(2,3-dihydrocinnamoyloxy)-3-methyl-2-butenyl]-5-prenylphenyl}-2-propenoic acid or those described by and incorporated by reference to Carvalho, et al., FOOD CHEMISTRY, 2011, 126(3), 1239-1245.

Brazilian green propolis, its oil extract or oil extract fractions (or its water or ethanol extracts), in some embodiments may be characterized or standardized based on a the phenylpropanoid 3-prenylcinnamic acid allyl ester ranging from about 23-29 wt %, preferably about 26.3%, and 20 to 20 wt % sesquiterpene spathulenol preferably about 23.4 wt %. Standardization may be based on the content of these or other compounds such as Drupanin, Artepillin C and Bacharin as they appear in raw propolis, its volatile components, or its fractions, such as its oil fraction, ethanol fractions or aqueous fractions.

Compositions comprising more than one BGP extract. In some embodiments, a mixture of water-ethanol, ethanol-oil, or water-oil extracts may be formulated, for example, at a ratio ranging from <12:1, 12:1, 10:1, 8:1, 6:1, 3:1, 2:1, 1:1, 1:2, 1:3, 1:6, 1:8, 1:10, or 1:12 or >1:12 (or any intermediate ratio or subrange of ratios). In another embodiment, such a mixture may contain two or three different propolis extracts, wherein each extract is present in an amount ranging from <5, 5, 10, 20, 30, 40, 50, 60, 70, 80, 90, 95 or >95 vol. %. Preferably, a combination of two or three different Brazilian green propolis extracts will produce a synergistic or additive anti-nociceptive effect on nociceptive, noninflammatory, or burn pain.

Inactive components. A BPG extract composition may contain other ingredients besides a BGP extract such as one or more carriers or excipients, for example, it may contain one or more emulsifiers or excipients, pH buffers, salts, preservatives, or antioxidants. The composition may be substantially hydrophobic, a mixture of hydrophobic and aqueous or polar components, or substantially aqueous or polar. Compositions include those containing mixtures of oils, water and water-miscible solvents, W/O or O/W emulsions, ointments or salves, pastes, liposomes, gels, foams, films, or varnishes may contain components of an ethanol and/or oil extract of BGP.

Compositions containing Brazilian green propolis ethanol extracts or BGP oil extract may include solvents (e.g., aqueous solvents), buffers, emulsifiers, surfactants, semi-solid or solid carriers, film-forming ingredients, propellants, or other excipients Emulsifiers include, but are not limited to, Agar, Albumin, Alginates, Casein, Ceatyl Alcohol, Cholic acid, Desoxycholic acid, Diacetyl tartaric acid esters, lecithin, and glycerol. Surfactants include, but are not limited to, ethoxylates, ethylene oxide/propylene oxide (EO/PO) copolymers, fatty alcohol ethoxylates, alkylphenol ethoxylates, and fatty acid ethoxylates. Preferably an emulsifier or surfactant commonly used in a skincare product is used.

Active components. A Brazilian green propolis extract composition may contain other active ingredients, such as analgesics including non-steroidal anti-inflammatory drugs (NSAIDs) such as salicylates and ibuprofen. Other analgesics may be incorporated including opioid receptor modulators, sodium channel blockers, calcium channel blockers TRP channel modulators, cannaboid receptor modulators, nerve growth factor inhibitors. Examples of these analgesics are incorporated by reference to hypertext transfer protocol secure://en.wikipedia.org/wiki/List_of_investigational_analgesics (last accessed Apr. 15, 2021). Preferably, a combination of Brazilian green propolis extracts with another active ingredient will produce a synergistic or additive effect on nociceptive, noninflammatory, or burn pain.

Skincare. A Brazilian green propolis extract composition may be incorporated into a skin protectant or skin restoring product, such as an ultraviolet protectant, sunscreen, sunblock or post-UV exposure protectant. These products typically contain one or more occlusive agents which create a barrier that blocks water from escaping the skin, such as petrolatum, mineral oil and/or dimethicone; one or more humectants, which are ingredients that attract water, such as glycerin or glycerates; and one or more emollients, such as coconut oil, cetyl esters, and silicones; which improve the feel of a protectant on the skin and reduce the tackiness and greasiness caused by the other moisturizing ingredients.

Sunscreen. In some embodiments at least one compound that screens out, filters, or blocks UV radiation may also be incorporated. Such compounds include para-aminobenzoic acid (PABA), padimate O, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium oxide, zinc oxide and mixtures thereof. In contrast to conventional sunscreens or sunblocks, the composition of the invention contains a Brazilian green propolis extract which further protects against nociceptive paid caused by exposure to harsh conditions, such as to directly sunlight on a beach.

In one embodiment, an ethanol and/or oil extract containing composition may be applied to a burn to prevent further aggravation of the burn or nociceptive pain or itching from the burn, for example, which is caused by subsequent exposure to UV or infrared light which induces pain or causes additional inflammation to a prior burn. The application of a BGP composition as disclosed herein to an existing burn can block new afferent pain signaling caused by subsequent aggravation of an existing burn by UV or infrared exposure, for example, by blocking new pain signaling transmitted via C fibers and other afferent myelinated fibers.

A composition comprising an ethanol and/oil extract as disclosed herein may be used in conjunction with laser or photodynamic therapy, for example, by its application to skin or tissue before, during or after such a therapy to avoid or mitigate pain.

In another embodiment of the present disclosure an individual suffering from a skin burn such as a first-degree or second-degree burn can be subject to treatment with light to further reduce pain caused by the burn. In this embodiment of the invention the skin area damaged by the burn, e.g., excessive exposure to sunlight and/or heat in amounts sufficient to cause a first or second degree burn, and exhibiting characteristic pain symptoms, is first treated with exposure to UV light prior to application of a BGP composition to the burn area. The application of UV light is carried out immediately prior to the application of the BGP composition, preferably within 30 minutes, 20 minutes, 10 minutes or 5 minutes prior to application of BGP composition. The application of UV light to a skin surface suffering a prior burn may lead to a minor aggravation or sensitization of the existing burn. However, the subsequent application of a BGP composition is especially effective for providing quick pain relief and almost immediately after application of the BGP composition, e.g., a patient treated in this manner may report no pain symptoms within 30 minutes, preferably 10 minutes or 5 minutes of application of the BGP composition. Preferably the UV light used to expose the burned skin surface is mainly within a wavelength of 280-400 nm, preferably 320-400 nm, which is typically regarded as including the UVA and UVB portions of the light spectrum. The effect of quick reduction in discomfort from pain is not as prevalent for treatment using secondary exposure to UVC light wavelengths.

The UV exposure is preferably of greater intensity for short periods of time. Preferably the UV exposure occurs briefly (over a period of time of 10 minutes or less, preferably five minutes or less) at levels of 1-50 milliwatt per square centimeter, preferably 10-40 mW/cm$^2$ or about 25 mW/cm$^2$ of direct exposure to UV light from a bulb that preferentially emits light in the UVB portion of the light spectrum.

Natural ingredients. A composition containing Brazilian green propolis water, ethanol or BGP oil extracts include essential oils such as *eucalyptus*, cedarwood, clove, *litsea cubeba, mentha arvensis*, rosemary, rose hips, garlic, sweet organe, sweet basil, melissa, cajeput, chamomile, wintergreen, turmeric, peppermint, menthol, camphor or lavendar oils; tea tree oil, hemp oil, coconut oil, palm oils, medium chain triglycerides, shea butter, jojoba oil, cocoa butter; or *capsicum* extracts such as capsaicin, dihydrocapsaicin, nor-dihydrocapsaicin, capsaicinoids, curcuminoids, gingerols, shogaols, zingerones, gingerdiols, or gingerdione. Other essential oils are described by and incorporated by reference to hypertext transfer protocol secure://en.wikipedia.org/wiki/Essential_oil (last accessed Apr. 15, 2021). Alternatively, other oily or hydrophobic ingredients such as petrolatum or mineral oil may be used in a composition comprising a BGP ethanol or oil extract.

Vitamins. The Brazilian green propolis water, ethanol, or oil extracts may be admixed with fat soluble vitamins such as vitamin A (retinoic acid, other retinoids, carotenes), D, E, K1 (phylloquinone) or K2 (menaquinone). Vitamin A functions to keep skin and mucous membranes health and promotes growth. Vitamin D is involved in bone and teeth health and strength. Vitamin is a fat soluble antioxidant which can protect cell membranes. Vitamin K is involved in blood clotting, maintaining bone health and preventing calcification of arterial and other tissues. These vitamins in combination with Brazilian green propolis water, ethanol or oil promote additive, complementary, or synergistic analgesic and/or regenerative effects. Emulsifiers or surfactants, such as those described below, may be included to facilitate admixture of hydrophobic and hydrophilic extracts or their components.

The Brazilian green propolis ethanolic extracts or BGP oil may also be admixed with water soluble vitamins such as the B vitamins like B1 (thiamine), B2 (riboflavin), B3 (niacin), B4 (adenine), B5 (panthothenic acid), B6 (pyroxidine), B7 (biotin), B8 (inositol), B9 (folate) and B12, or vitamin C (ascorbic acid, ascorbyl palmitate). Gamma-aminobutyric acid may be included in some combinations. Vitamins B1, B6, B12 and GABA in addition to their effects on nociceptive or non-inflammatory nociceptive pain may reduce neuropathic pain. Emulsifiers or surfactants may be included to facilitate admixture of hydrophilic and hydrophobic extracts or their components.

Co administration of the vitamins or nutrients described above can reduce or eliminate nociceptive pain or non-inflammatory nociceptive pain as well as promote healing of damaged skin, mucous membranes or other distressed tissues. Such methods and compositions may be applied to treatment of neuropathy, such as diabetic neuropathy, and chronic pain.

In some embodiments, the Brazilian green propolis ethanol extracts or BGP oil extracts incorporate fluids used in medicine or dentistry such as saline solutions, rinses, lavage fluids, dialysis fluids, or artificial saliva. Brazilian green propolis ethanol extracts or BGP oil extracts may be incorporated into a microparticle or nanoparticle; a gel, foam, or spray; an emulsion, liposome, ointment, paste, salve; or a film.

Routes of administration. The methods of administering the BGP extracts or compositions containing them disclosed herein may comprise administering a silver or titanium oxide nanoparticle composition or composition intravenously, intramuscularly, topically (e.g. on or into a wound or lesion), intradermally, into or over a wound, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intraarticularly, into a bursa, subpericardially, into an axilla, intrauterine, into the pleural space, intraperitoneally, transmucosally, or transdermally.

Carriers/Excipients. The term carrier encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9% or mixtures of normal saline with glucose or mannose. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety.

Formulations for administration. For therapeutic purposes, formulations for parenteral administration of compositions comprising BGP extracts can be in the form of aqueous or non-aqueous isotonic sterile injection solutions or suspensions. The term parenteral, as used herein, includes intravenous, intravesical, intraperitoneal, subcutaneous, intramuscular, intralesional, intracranial, intrapulmonal, intracardial, intrasternal, and sublingual injections, or infusion techniques.

Topical administration. Formulations for topical administration to the skin, wounds, burns, or mucous membranes include, for example, ointments, creams, gels and pastes comprising the composition in a pharmaceutical acceptable carrier. The formulation of the composition for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Oral administration. Solid preparations for oral administration may include a tablet, a pill, a powder, a granule, a capsule, and the like. These solid preparations may be prepared by mixing at least one excipient, such as starch, calcium carbonate, sucrose, lactose, or gelatin, with nanoparticle as disclosed herein. In addition to such a simple excipient, lubricants, such as magnesium stearate and talc, may be used. Liquid preparations containing BGP extracts for oral administration correspond to a suspension, a liquid for internal use, oil, syrup, and the like, and may include several types of excipient, for example, a wetting agent, a sweetener, an aroma, a preservative, and the like, in addition to simple diluents that are frequently used, such as water and liquid paraffin.

Parenteral administration. Injectable preparations, for example, sterile injectable aqueous or oleaginous suspensions containing BGP extract can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Respiratory system administration. Administration to the respiratory system may be accomplished using a drug delivery device such as a nebulizer to administer a nanoparticle composition as disclosed herein, in an inhalable form. Nebulizers include soft mist inhalers, jet nebulizers, ultrasonic wave nebulizers, and nebulizers using vibrating mesh technology. A metered-dosage inhaler is another drug delivery device that delivers a selected or metered amount of a medication, such as the nanoparticle compositions disclosed herein. Typically, this device produces and releases an aerosol of micrometer-sized particles that are inhaled. The aerosol will comprising a BGP extract or component thereof as disclosed herein and may contain excipients or carriers.

Thus, preferably, particles comprising an extract are sized so as to provide a uniform dosage or so they are absorbed in a particular part of the respiratory system. In some cases, the particles may be a dry powder in others as a mist or in a semiliquid form. Metered-dose inhalers and their various components, propellants, excipients and other elements are described by and incorporated by reference to hypertext transfer protocol secure://en.wikipedia.org/wiki/Metered-dose_inhaler. An inhalable composition may be formulated in the form of a hydrofluoroalkane inhaler or HFA (metered dose inhaler or MDI), dry powder inhaler (DPI), or as a nebulizer solution.

Dose. The dose of a BGP extract as disclosed herein with respect to the human or animal body may vary depending on patient's age, body weight, and gender, the form of administration, state of health, and severity of disease. The dose may be generally 0.01-100 mg/kg/day, preferably 0.1-20 mg/kg/day, and more preferably 5-10 mg/kg/day. The composition may also be divisionally administered at predetermined intervals according toconverted or adjusted based on body surface area, e.g., to mg/m$^2$. Such adjustments or conversions may be calculated using formulas known in the art; see DuBois D & DuBois E F. *A formula to estimate the approximate surface area if height and weight be known.* ARCH INTERN MEDICINE. 1916; 17:863-71; and Wang Y, Moss J, Thisted R. *Predictors of body surface area.* J CLIN ANESTH. 1992; 4(1):4-10, both of which are incorporated by reference.

An amount of BGP ethanol or oil extraction to be applied to a tissue or skin surface may be selected by one skilled in the medical or pharmaceutical arts. It may be based on the topical application of a particular concentration of an ethanol or oil extract contained in a topically-applied composition, for example, application of a composition containing a concentration of BGP ethanol or oil extract ranging from 0.01, 0.1, 0.2, 0.5, 1, 2, 5, 10, 50 to 100 vol/vol. % of the extract. In other embodiments, the concentration of the extract is based on its dry or residual content after removal of the solvent, such as removal of ethanol and water from an ethanol extract, or removal of oil from an oil extract. For example, a topical product may contain from 0.001, 0.002, 0.005, 0.01, 0.02, 0.05, 0.1, 0.2, 0.5, 1, 2, 5, 10 or >10 mg/kg or mg/L of the dry or residual extract after solvent removal.

Nociceptive pain. Nociception is the sensory nervous system's process of encoding noxious stimuli. In nociception, intense chemical (e.g., cayenne powder), mechanical (e.g., cutting, crushing), or thermal (heat and cold) stimulation of sensory nerve cells called nociceptors produces a signal that travels along a chain of nerve fibers via the spinal cord to the brain. Nociception triggers a variety of physiological and behavioral responses and usually results in a subjective experience, or perception, of pain in sentient beings. Potentially damaging mechanical, thermal, and chemical stimuli are detected by nerve endings called nociceptors, which are found in the skin, on internal surfaces such as the periosteum, joint surfaces, and in some internal organs. Some nociceptors are unspecialized free nerve endings that have their cell bodies outside the spinal column in the dorsal root ganglia. Other nociceptors rely on specialized structures in the skin to transduce noxious information such as nociceptive schwann cells. Nociceptors are categorized according to the axons which travel from the receptors to the spinal cord or brain. After nerve injury it is possible for touch fibers that normally carry non-noxious stimuli to be perceived as noxious.

Nociceptors have a certain threshold; that is, they require a minimum intensity of stimulation before they trigger a signal. Once this threshold is reached a signal is passed along the axon of the neuron into the spinal cord.

Nociceptive threshold testing deliberately applies a noxious stimulus to a human or animal subject in order to study pain. In animals, the technique is often used to study the efficacy of analgesic drugs and to establish dosing levels and period of effect. After establishing a baseline, the drug under test is given and the elevation in threshold recorded at specified time points. When the drug wears off, the threshold should return to the baseline (pre-treatment) value.

Potentially damaging mechanical, thermal, and chemical stimuli are detected by nerve endings called nociceptors, which are found in the skin, on internal surfaces such as the periosteum, joint surfaces, and in some internal organs. Some nociceptors are unspecialized free nerve endings that have their cell bodies outside the spinal column in the dorsal root ganglia. Other nociceptors rely on specialized structures in the skin to transduce noxious information such as nociceptive schwann cells. Nociceptors are categorized according to the axons which travel from the receptors to the spinal cord or brain. After nerve injury it is possible for touch fibers that normally carry non-noxious stimuli to be perceived as noxious.

Nociceptors have a certain threshold; that is, they require a minimum intensity of stimulation before they trigger a signal. Once this threshold is reached a signal is passed along the axon of the neuron into the spinal cord. Nociceptive threshold testing deliberately applies a noxious stimulus to a human or animal subject in order to study pain. In animals, the technique is often used to study the efficacy of analgesic drugs and to establish dosing levels and period of effect.

Pain. The sensation of pain is associated with the activation of the receptors in the primary afferent fibers, which is inclusive of the unmyelinated C-fiber and myelinated Aa-fiber. Both nociceptors remain silent during homeostasis in the absence of pain and are activated when there is a potential of noxious stimulus. The perception of a series of sensory events is required for the brain in order to detect pain and produce a response towards the threat. There are generally three main stages in the perception of pain. The first stage is pain sensitivity, followed by the second stage where the signals are transmitted from the periphery to the dorsal horn (DH), which is located in the spinal cord via the peripheral nervous system (PNS). Lastly, the third stage is to perform the transmission of the signals to the higher brain via the central nervous system (CNS). Typically, there are two routes for signal transmissions to be conducted: ascending and descending pathways. The pathway that goes upward carrying sensory information from the body via the spinal cord towards the brain is defined as the ascending pathway, whereas the nerves that goes downward from the brain to the reflex organs via the spinal cord is known as the descending pathway. Nociceptive pain is the normal response to noxious (intense) stimulation.

C-fiber mediated pain. Group C nerve fibers are one of three classes of nerve fiber in the central nervous system (CNS) and peripheral nervous system (PNS). The C group fibers are unmyelinated and have a small diameter and low conduction velocity, whereas Groups A and B are myelinated. Group C fibers include postganglionic fibers in the autonomic nervous system (ANS), and nerve fibers at the dorsal roots (IV fiber). These fibers carry sensory information. Damage or injury to nerve fibers causes neuropathic pain. Capsaicin activates C fiber vanilloid receptors, giving chili peppers a hot sensation. Besides non-myelinated C fibers, pain may be afferently transmitted via thinly myelinated A-sigma, medium myelinated A-beta, or thickly mediated A-alpha fibers.

NMDA receptor mediated pain. Receptors called "N-methyl-D-aspartate receptors" (NMDA receptors) have been shown to mediate chronic pain and visceral pain, including the pain from distending a balloon in the colon. These receptors are expressed in the spinal column and in peripheral tissues.

Nitric oxide and inflammatory pain. Nitric oxide (NO) is a signaling molecule that plays a key role in the pathogenesis of inflammation. It gives an anti-inflammatory effect under normal physiological conditions. On the other hand, NO is considered as a pro-inflammatory mediator that induces inflammation due to over production in abnormal situations. NO is synthesized and released into the endothelial cells by the help of NOSs that convert arginine into citrulline producing NO in the process. Oxygen and NADPH are necessary co-factors in such conversion. NO is believed to induce vasodilatation in cardiovascular system and furthermore, it involves in immune responses by cytokine-activated macrophages, which release NO in high concentrations. In addition. NO is a potent neurotransmitter at the neuron synapses and contributes to the regulation of apoptosis. NO is involved in the pathogenesis of inflammatory disorders of the joint, gut and lungs.

Inflammatory pain refers to increased sensitivity due to the inflammatory response associated with tissue damage. Under these sensitized conditions, an innocuous stimulus can be perceived as painful—this is known as allodynia—and the pain evoked by a noxious stimulus is exaggerated in both amplitude and duration—this is known as hyperalgesia. Inflammatory pain is a type of nociceptive pain that results from activation and sensitization of nociceptors by inflammatory mediators or increased sensitivity due to the inflammatory response associated with tissue damage.

Primary hyperalgesia is a direct consequence of peripheral sensitization, the process whereby inflammatory mediators and other local factors-prostaglandin, bradykinin, cytokines (e.g, interleukin), histamine, serotonin, protons, potassium, ATP, glutamate, and so on-trigger intracellular signaling pathways in the peripheral terminals of primary afferents, leading to changes in the function and/or expression of receptor molecules and voltage-gated ion channels, which ultimately causes those afferents to become hyperresponsive to stimulation. Notably, peptidergic C fibers can release substance P and calcitonin gene-related peptide (CGRP) from their peripheral terminals, causing neurogenic inflammation, thus forming a nasty positive feedback loop. Through a phenomenon known as an axon reflex, in which spikes initiated in one fiber branch propagate antidromically down neighboring fiber branches, neurogenic inflammation can extend throughout the receptive field of a peptidergic C fiber. The hypersensitivity can spread even further through the effects of central sensitization, which involves synaptic plasticity and other changes in the downstream central circuits. Synaptic plasticity and numerous other changes contribute to making the pain persistent but, generally speaking, inflammatory pain persists only as long as the inflammation. Reducing the inflammation is therefore a logical way to reduce the pain. Nonsteroidal anti-inflammatory drugs (NSAIDs), such as aspirin block the synthesis of prostaglandins and thromboxanes via the enzyme cyclooxygenase. Further description of pain is described by and incorporate by reference to, hypertext transfer protocol secure://www.sciencedirect.com/topics/medicine-and-dentistry/inflammatory-pain hypertext transfer protocol secure://www.sciencedirect.com/topics/medicine-and-dentistry/nociceptive-pain. Other types of pain include traumatic pain, arthritic pain, and post-operative pain which are described by and incorporated by reference to hypertext transfer protocol secure://www.sciencedirect.com/topics/medicine-and-dentistry/inflammatory-pain. The compositions and methods disclosed herein may be applied to treatment of such types of pain.

Burns. The treatment of burns depends on the depth, area and location of the burn. Burn depth is generally categorized as first, second or third degree. A first degree burn is superficial and has similar characteristics to a typical sun burn. The skin is red in color and sensation is intact. In fact, it is usually somewhat painful. Second degree burns look similar to the first degree burns; however, the damage is now severe enough to cause blistering of the skin and the pain is usually somewhat more intense. In third degree burns the damage has progressed to the point of skin death. The skin is white and without sensation. The methods and compositions disclosed herein may be used to treat first, second or third degree burns, for example, by the application of a composition or burn dressing containing BGP ethanol and/or oil extract. In some cases, treatment will comprise prophylactic administration of a composition comprising BGP ethanol or BGP oil extract.

At the time of burn injury, tissue damage is the primary mechanism of pain. Stimulation of local nociceptors transmits an impulse via Ad and C fibers to the dorsal horn of the spinal cord. Peripheral sensory nerves and descending influences from cortical areas can modulate the magnitude of the pain impulse. Ultimately, conscious perception of pain is regulated by areas of the brain often named the "pain matrix" which is thought to involve a network of higher cortical areas and the thalamus. The conscious perception of pain is affected not only by the burn wound itself but also by context, cognition, pharmacologics, mood and other predisposing factors. Burn pain may also vary and fluctuate widely over the span of recovery. Therefore, the successful treatment of burn pain should involve a multi-modal approach tailored to the patient and scenario. These and other features of burns and burn pain are described by and incorporated by reference to Griggs, C. et al., CLIN PLAST SURG. 2017 July; 44(3): 535-540. Prevention or immediate treatment of early events in nociception of burn and other types of nociceptive pain may reduce subsequent perception of other types of pain, such as inflammatory pain.

The mechanisms underlying burn-induced neuropathic pain have not been studied in detail. Acute pain arises from a range of noxious stimuli including heat, cold, mechanical stimuli, and chemicals. In the case of burn-induced pain, damage to peripheral sensory neurons and inflammatory processes initiated by the injury exacerbate this acute response and transform burn pain into a complex symptom comprising multiple components, including ongoing background pain and procedural pain during surgical interventions and dressing changes. In addition, burn-induced pain can persist beyond the initial injury and develop into chronic pain with neuropathic features. However, the long list of the biological ad pharmacological properties could make propolis a good analgesic agent for different type of pains including burn pain. Biochemical and clinical features of burn pain are described by, and incorporated by reference to, Morgan, et al, *Burn Pain: A Systematic and Critical Review of Epidemiology, Pathophysiology, and Treatment*, PAIN MEDICINE, 2017, 19(4), 708-734, In preferred embodiments, the compositions and methods disclosed herein are used to treat one or more features or symptoms of burn pain.

The methods and compositions disclosed herein may be used to interrupt early events in nociception of burn pain as well as subsequently reduce the development or perception of inflammatory pain. A burn results in complicated chemical and immunological inflammatory response that can be restricted to the site of injury or involve systemic inflammatory processes. Activation of peripheral sensory nerve terminals after burn injuries as well as sustained nociceptive input post-injury can occur through a range of stimuli, including the initial thermal insult, vascular damage, hypoxia from ischemic events. DAMP receptor activation, and local release of pro-inflammatory and algogenic mediators and transmitters such as bradykinin, histamine, eicosanoids, platelet-activating factor (PAF), nerve growth factor (NGF), Substance P. and CGRP, trigger a syndrome associated with significant morbidity and mortality. Further description of these phenomena are described by, and incorporated by reference to Morgan, et al., supra. The compositions and methods disclosed herein may interrupt or attenuate one or more of these phenomena.

Assays for evaluating or measuring nociceptive pain include those described in the Examples as well as those described by, and incorporated by reference to, hypertext transfer protocol secure://en.wikipedia.org/wiki/Nociception_assay (last accessed Jun. 1, 2021). A nociception assay (nocioception or nocioperception assay) evaluates the ability of an animal, usually a rodent, to detect a noxious stimulus such as the feeling of pain, caused by stimulation of nociceptors. These assays measure the existence of pain through behaviors such as withdrawal, licking, immobility, and vocalization. In animals (rats), signs of pain are measured by quantifiable behavioral components; examples of such behaviors include paw withdrawal latency in reaction to thermal noxious stimulation (heat, cold), frequency and threshold of paw withdrawal in reaction to mechanical stimulation, degree of self-mutilation (autotomy), or spontaneous lifting and licking of paws. These reactions are interpreted as equivalent to mechanical or thermal hyperalgesia or allodynia or spontaneous pain in humans.

EXAMPLE

Methodology. Experimental Animals. Wistar male albino rats (250-300 g) were obtained from the animal house of the Imam Abdulrahman Bin Faisal University. Animals were maintained with free access to water and food at controlled room temperature 25-29° C., 12-h light and 12 h darkness cycles"; Al-Hariri, M. T.; et al., *Protective effect and potential mechanisms of propolis on streptozotocin-induced diabetic rats*. J. TAIBAH UNIV. MED SCI. 2016, 11, 7-12, incorporated herein by reference in its entirety. The experiment was performed after approval of the protocols by University Institutional Review Board Committee (IRB 2015-03-114) and was carried out in accordance with the current guidelines for the care of laboratory animals.

Rats were distributed into three random groups (n=6);

Group I is a control group that received normal saline intraperitoneally (i.p.);

Group II was treated with high flavonoids Brazilian green propolis (55%) ethanol extracts (Uniflora) 50 mg/kg (P50) i.p. and Group III was treated with 100 mg/kg (P100) i.p.

Animal groups were treated 60 min before testing; Deuis, J. R. et al., Methods used to evaluate pain behaviors in rodents. FRONT. MOL. NEUROSCI. 2017, 10, 284, incorporated herein by reference in its entirety.

Animal Models of Pain include the tests and assays which are described below.

Thermal Hyperalgesia (Infrared) Test. Thermal hyperalgesia was assessed using a planter analgesic meter (Ugo Basile, Gemonio, Italy). Rats were placed individually in clear plastic cages and allowed to acclimate for 20 min before testing. The center of a focused beam of infrared heat was applied to the plantar surface of the hind paws. Both timer and bulb were immediately turned off by rat's paw withdrawal or on reaching a predetermined cut-out (usually 22 s) to prevent tissue damage. The reaction time was recorded when the rats licked their hind paws and jumped at several intervals of 30, 60 and 90 min post propolis administration. The withdrawal latency of hind paws was measured to the nearest 0.1 s. See Deuis, J. R. & Vetter, I. *The thermal probe test: A novel behavioral assay to quantify thermal paw withdrawal thresholds in mice*. TEMPERATURE 2016, 3, 199-207, incorporated herein by reference in its entirety.

Formalin Test. Rats were treated with different doses (P50 and P100) of propolis i.p. After sixty minutes, 50 μL of 5% formalin was injected subcutaneously into the dorsal surface of the right hind paw using a microsyringe with a 27-gauge needle. Immediately after formalin injection, the animals were placed individually in acrylic observation chambers (320 cm×40 cm). Mirrors were arranged at angles to allow clear observation of the paws of the animals. Each rat in every group was observed simultaneously from 0 to 60 min following formalin injection.

The nociceptive response was identified by counting the number of flinches of the injected paw. The number of flinches was counted for the periods of 0-5 min (neurogenic phase) and 10-60 min (Inflammatory phase). See Hong, J.-S.; et al. *Antinociceptive effect of chrysin in diabetic neuropathy and formalin-induced pain models*. ANIM. CELLS SYST. 2020, 24, 1-8, incorporated herein by reference in its entirety.

Abdominal Writhing test. Abdominal writhe (contraction) was induced by i.p. injection of 1 mL of a solution of 2% acetic acid using a 25-gauge injection needle. Five minutes after the administration of acetic acid, the frequencies of abdominal writhing were recorded for sixty minutes and, the latent period, i.e., beginning of the first abdominal writhe after injection, was also observed. See Bahamonde et al., *Antinociceptive and anti-inflammatory activities of an aqueous extract of Chiliotrichum diffusum*, REVISTA BRASILIERA DE FARMACOGNOSIA, 2013, 23(4), 699-705; incorporated by reference.

Statistical Analysis. Statistical analysis was performed using the Statistical Package for the Social Sciences (IBM SPSS V 21). The normality of data were tested by the Shapiro-Wilk. The number of flinches of all phases of response were calculated for each rat. Data with homogeneity of variance were analyzed using the two-way analysis of variance (ANOVA), and multiple post hoc comparisons were performed using the Tukey's test. p-values <0.05 were considered to be statistically significant. Data were expressed as mean±standard error of mean (SEM).

Figure 1:
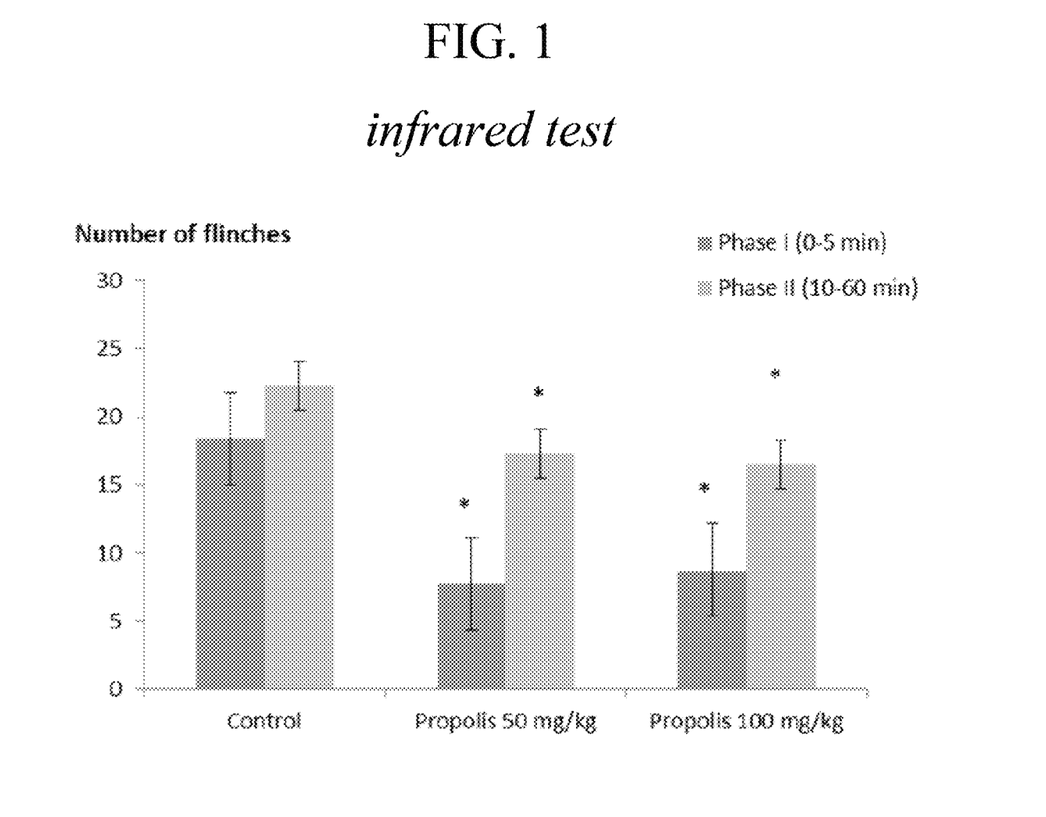
FIG. 1 is a bar graph illustrating the antinociceptive effect of Brazilian green propolis alcohol extract (P50 and P100) in the infrared test in the rats. The values expressed are mean t SEM, (n=6).*$p<0.05$: significantly different for treated (P50 and P100) compared to the control groups as determined by ANOVA analysis followed by multiple comparison post hoc tests.

Inhibitory Effect of Propolis on Thermal Stimuli-Induced Nociception in the Infrared Test. Administration of Brazilian green propolis alcohol extract at doses 50 and 100 mg/kg, i.p. increased the latency time to the nociceptive response in the infrared test. Significant differences (p<0.05) between the mean thermal threshold of P50 and P100 than the control, clearly indicating the analgesic property of the alcohol Brazilian green propolis alcohol extract as presented in FIG. 1.

Figure 2:
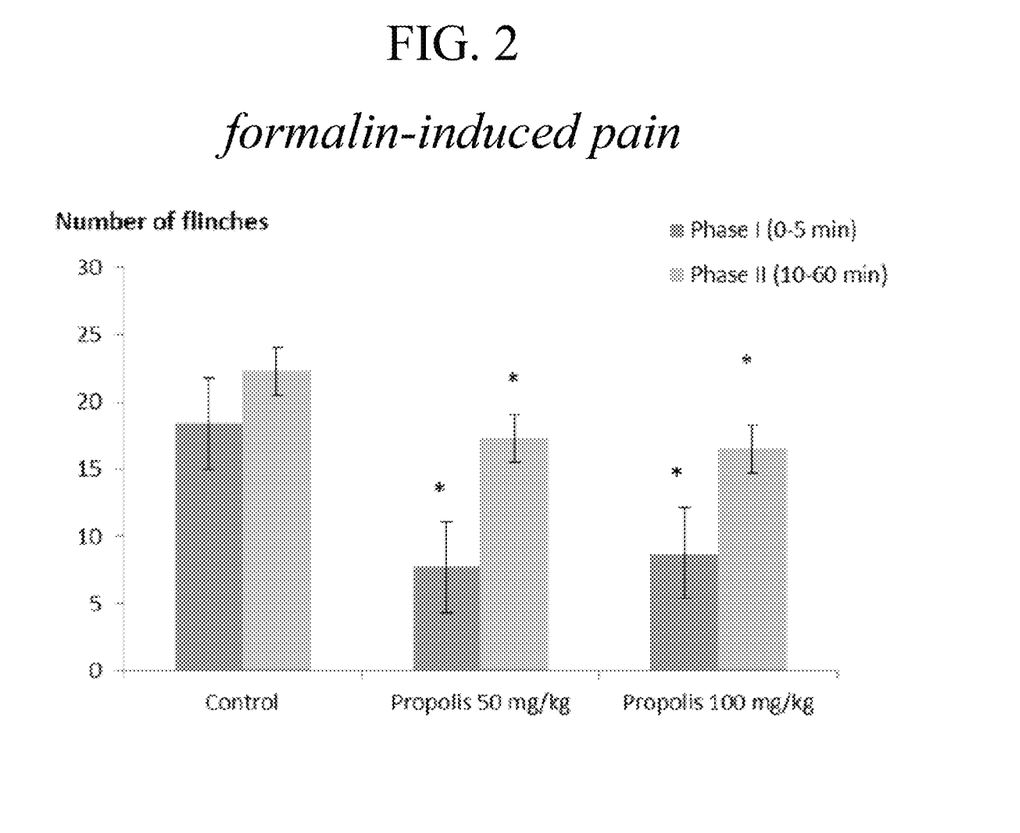
FIG. 2 is a bar graph illustrating the effect of Brazilian green propolis alcohol extract (P50 and P100) in the formalin-induced nociception model: neurogenic (Phase I) and inflammatory (Phase II). The values expressed are mean t SEM, (n=6). *$p<0.05$: significantly different for treated (P50 and P100) compared to the control groups as determined by ANOVA analysis followed by multiple comparison post hoc test.

Inhibitory Effects of Propolis on Formalin-Induced Inflammatory Nociception. FIG. 2 shows the effect of the Brazilian green propolis alcohol extract on formalin-induced pain during the acute phase in rats. Both propolis groups (P50 and P100) displayed a significant (p<0.05) reduction in formalin-induced nociceptive behavior monitored by the mean number of flinches across all time points of the neurogenic phase (0-5 min) than the control. Similarly, a significant (p<0.05) pain inhibition in both groups (P50 and P100) was observed in the inflammatory phase (10-60 min) after induction of the noxious stimulus, than the control.

Figure 3:
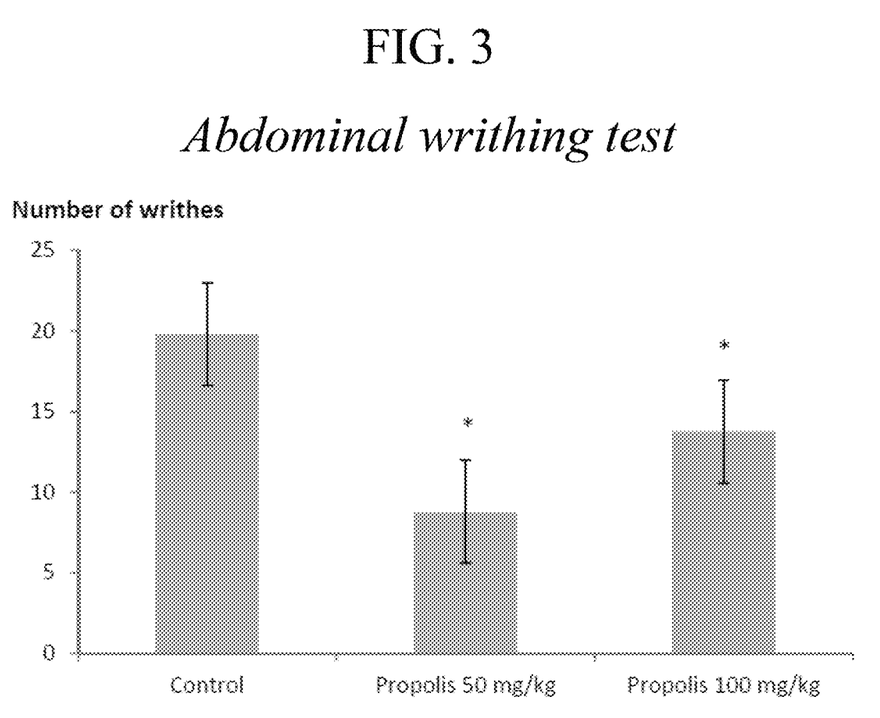
FIG. 3 is a bar graph illustrating the effect of Brazilian green propolis alcohol extract (P50 and P100) against acetic acid-induced abdominal contraction in rats. The values expressed are mean t SEM (n=6). *$p<0.05$: significantly different for treated (P50 and P100) compared to the control groups as determined by ANOVA analysis followed by multiple comparison post.

Inhibitory Effect of Propolis on Acetic Acid-Induced Writhing Response. The effect of the Brazilian green propolis ethanol extract on the antinociceptive activity as determined by the acetic acid-induced abdominal writhing test is shown in FIG. 3. Both the 50 and 100 mg/kg, i.p. does of the BGO ethanol extract significantly (p<0.05) decreased acetic acid-induced writhing responses compare to responses in the control group.

The data presented above show that administration of BGP ethanol extract significantly reduced nociceptive responses as determined several well-established in vivo nociception assays which measure different pain stimuli including both chemical and thermal pain stimuli. Administration of Brazilian green propolis alcohol extract reduced the number of flinching response evoked by formalin injection during both phases. The early phase started at the time of injection and lasted for about five minutes and the late phase, which started at 10 minutes post-injection and lasted for about 60 minutes. The early phase response results from immediate stimulation of primary afferent fibers (C-fiber activation due to the peripheral stimulus) in the paw that reflects the centrally mediated pain. The late phase response may result from an inflammatory reaction in the peripheral tissue, combined with the activation of wide dynamic range neurons (activation of N-methyl-D-aspartate (NMDA) and non-NMDA receptors and NO cascade) in the dorsal horn of the spinal cord. Further description of these responses and pain stimuli are incorporated by reference to Hunskaar, S. & Hole, K. *The formalin test in mice: Dissociation between inflammatory and non-inflammatory pain*. PAIN 1987, 30, 103-114; and Puig, S.; Sorkin, L. *Formalin-evoked activity in identified primary afferent fibers: Systemic lidocaine suppresses phase-2 activity*. PAIN 1996, 64, 345-355.

The inventors considered that Brazilian green ethanol extract possesses a biphasic analgesic effect. As shown above, Brazilian green propolis ethanol extract causes a significant inhibition of acetic acid-induced pain that reduced the number of abdominal contraction and stretching of hind limbs. While not being bound to any theory or technical explanation, this acetic acid induced nociceptive response may involve both the synthesis of inflammatory mediators which reduce the threshold of nociception and the direct stimulation of the nociceptive afferent fibers due to the reduction of pH. Moreover, the antinociceptive effect of Brazilian green propolis alcohol extract against acetic acid-induced writhing may occur via local peritoneal receptors or by inhibition of prostaglandin synthesis or action.

As shown and disclosed herein, the inventors have found that a BGP ethanol extract exhibits an important analgesic effects including inhibition of pain threshold. These results demonstrate that an extract of a natural product, BGP, may be used in the treatment of several painful and/or inflammatory diseases or conditions, especially in the management of nociceptive pain associated with thermal injury.

The invention claimed is:

1. A method for treating nociceptive pain from a burn, comprising:
    administering to a subject in need of treatment for nociceptive pain from a burn afferently transmitted via non-myelinated C fibers a composition comprising an ethanol extract of Brazilian green propolis ("BGP"),
    wherein the ethanol extract of BGP is produced by extracting BGP with an aqueous solution of 60 to 80% ethanol,
    wherein the BGP contains 40-60 wt. % flavonoids and phenolic acids,
    wherein the extraction is carried out at a pH between about 6 and about 8,
    wherein the composition comprises 1.0 to 5 wt % Artepillin C, 1-5 wt % drupanin, 1-5 wt % baccharin, and less than 0.01 wt % formononetin;
    wherein the dose is administered subcutaneously by injection;
    wherein the dose ranges from 50 to 100 mg/kg/day; and
    wherein the early phase neurogenic analgesic response is stronger at a dose of 50 mg/kg than the response at 100 mg/kg.

2. The method of claim 1, wherein the pain from the burn is non-inflammatory pain.

3. The method of claim 1, wherein the nociceptive pain is an early phase response mediated by myelinated A-sigma, A-beta, or A-alpha fibers.

4. The method of claim 1, wherein the nociceptive pain further comprises late phase response resulting from an inflammatory response in combination with activation of N-methyl-d-aspartate (NMDA) and non-NMDA receptors and NO cascade.

5. The method of claim 1, wherein the ethanol extract of BGP is produced by extracting BGP with an aqueous solution of at least 70% ethanol.

6. The method of claim 1, wherein the composition further comprises an oil extract of BGP.

7. The method of claim 1, wherein the composition further comprises a vegetable oil extract of BGP.

8. The method of claim 1, wherein the composition further comprises a vegetable oil extract of BGP that has been emulsified with the ethanol extract of BGP.

9. The method of claim 1, where the composition further comprises a NSAID or an opioid.

10. The method of claim 1, further comprising exposing at least a portion of the burn of the subject in need of treatment to UV light at an intensity of 5-50 mW/cm$^2$ for up to ½ hour ½ hour or less prior to administering the composition comprising the BGP ethanol extract to the burn, wherein the UV light is in a wavelength range of 280-400 nm.

* * * * *